United States Patent [19]

Kozarich et al.

[11] Patent Number: 4,710,566
[45] Date of Patent: Dec. 1, 1987

[54] PURIFICATION OF THE MESSENGER RNA CAP-BINDING PROTEIN

[75] Inventors: John W. Kozarich, College Park, Md.; Robert E. Rhoads, Lexington, Ky.

[73] Assignee: Yale University, New Haven, Conn.

[21] Appl. No.: 686,708

[22] Filed: Dec. 27, 1984

[51] Int. Cl.$^4$ .................. C07H 19/06; C07H 19/10; C07H 19/16
[52] U.S. Cl. ........................................ 536/28; 536/29; 530/827
[58] Field of Search ............................ 536/27, 28, 29; 260/112 R; 530/827

[56] References Cited

U.S. PATENT DOCUMENTS

| | | | |
|---|---|---|---|
| 4,012,570 | 3/1977 | Dean et al. | 536/27 |
| 4,322,410 | 3/1982 | Stjepanovic et al. | 536/27 |
| 4,401,759 | 8/1983 | Rubin et al. | 536/29 |
| 4,500,707 | 2/1985 | Caruthers et al. | 536/29 |

*Primary Examiner*—Ronald W. Griffin
*Attorney, Agent, or Firm*—Walter J. McMurray

[57] ABSTRACT

The synthesis of a new affinity medium, the p-aminophenyl-γ-ester of 7-methylguanosine-5'-triphosphate coupled to Sepharose, for use in affinity chromatography is claimed. An improved method in terms of speed and purity for the isolation of messenger ribonucleic acid cap-binding protein is claimed. The synthesis of the p-aminophenyl-γ-ester of 7-methylguanosine-5'-triphosphate is described.

3 Claims, 5 Drawing Figures

PURIFICATION OF THE MESSENGER RNA CAP-BINDING PROTEIN

RIGHTS STATEMENT

The U.S. Government has a paid-up license in this invention and the right in limited circumstances to require the patent owner to license others on reasonable terms as provided for by the terms of Grant Nos. GM20818 and GM26985 from the National Institute of General Medical Sciences.

BACKGROUND OF THE INVENTION

This invention describes a family of affinity media for use in affinity chromatography. Specifically, this invention describes the synthesis of a new affinity medium, the p-aminophenyl-γ-ester of 7-methylguanosine-5'-triphosphate coupled to Sepharose, for use in affinity chromatography. This invention also describes an improved method for the isolation of messenger ribonucleic acid capbinding protein (CBP). CBP isolated by the improved method can be obtained in higher yield, and, to the limited extent to which it has been tested, has greater activity than CBP isolated with earlier methods.

CBP is a 24 kd (kilodalton) protein which binds specifically to messenger ribonucleic acid (m-RNA). CBP has been purified by conventional methods of protein fractionation. Hellmann et al. ((1982), J. Biol. Chem. 257, 4056) used a procedure which involved saturating rabbit reticulocyte ribosome extracts with ammonium sulfate, chromatography of the precipitate on diethylaminoethyl (DEAE)—cellulose, centrifugation on sucrose gradients containing 100 and 500 mM KCl, and column chromatography on DEAE—cellulose and phosphocellulose. Trachsel et al. ((1980) Proc. Natl. Acad. Sci. U.S.A. 77, 770) utilized ammonium sulfate fractionation, centrifugation on sucrose gradients containing 100 and 500 mM KCl, phosphocellulose chromatography, affinity chromatography with a medium of eIF-3 (an initiation factor) coupled to Sepharose 4B and phospho-cellulose chromatography to purify the CBP. The speed and simplicity of the isolation and purification of cap-binding protein would be greatly improved if affinity chromatography alone could be employed. Two reports have described the synthesis of different affinity media for the purification of CBP.

Sonenberg et al. ((1979), Proc. Natl. Acad. Sci. U.S.A. 76, 4345) coupled the levulinic acid acetal of 7-methylguanosine diphosphate (m$^7$GDP) to Sepharose (FIG. 1, resin 1), and Rupprecht et al. ((1981), Biochemistry 20, 6570), a 7-carboxypentyl derivative of GDP (FIG. 1, resin 2). Both were capable, with limitations, of specifically purifying the 24-kd CBP. Sonenberg et al. reported that application of a 0–40% ammonium sulfate fraction of the ribosomal salt wash to resin 1 did not yield any polypeptides upon elution with m$^7$GDP. It was necessary to first remove eIF-3, another peptide which binds CBP, by sucrose gradient centrifugation before application of extracts to the affinity material if the CBP was to be obtained. Rupprecht et al. also reported that not all of the CBP could be eluted with m$^7$GDP from resin 2; a considerable amount was present in the 1.0M KCl wash which followed. Therefore, while affinity chromatography with the above media reduces the number of steps required to purify CBP, some prepurification of the ribosomal salt washes is required if non-specific binding is to be minimized.

SUMMARY OF THE INVENTION

This invention describes a new method for isolating and purifying CBP. The new method utilizes affinity chromatography with a new affinity medium. This invention describes the preparation of this new affinity medium and its use in affinity chromatography. The new affinity medium is formed by coupling the p-aminophenyl-γ-ester of 7-methylguanosine-5'-triphosphate with Sepharose.

An object of the present invention is to develop a medium for affinity chromatography which would facilitate the isolation of CBP by reducing the number of prepurification operations prior to affinity chromatography. Another object of the present invention is to develop a medium for affinity chromatography which would result in the isolation of CBP in higher yield and activity than is attainable with earlier methods.

Another object of the present invention is to develop a medium for affinity chromatography suitable for the isolation and purification of CBP which is easily synthesized in high yield with a single isomeric structure. Another object of the present invention is to develop a medium for affinity chromatography which is chemically and enzymatically stable when employed as a medium for affinity chromatography. Another object of the present invention is to develop a technique for the isolation and purification of CBP.

DETAILED DESCRIPTION OF INVENTION

Figure 1:
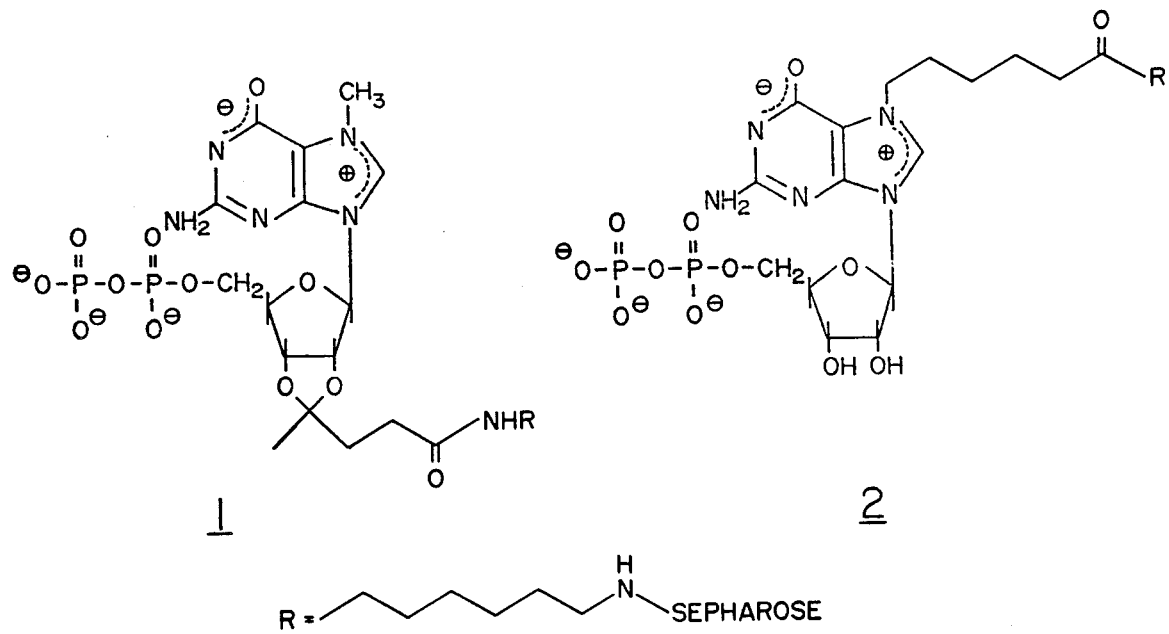
FIG. 1 presents structural representations of affinity resins for the purification of CBP. Compound 1 is 2',3'-0-[-1-(2-carboxyethyl)ethylidene]-7-methylguanosine-5'-diphosphate coupled to Sepharose (Sonenberg et al., 1979) 2 is 7-(5carboxypentyl)guanosine-5'-diphosphate coupled to Sepharose (Rupprecht et al., 1981) and 3 p-aminophenyl-γ-ester of 7-methylguanosine-5'-triphosphate coupled to Separose. (See Specification.)
Figure 1:
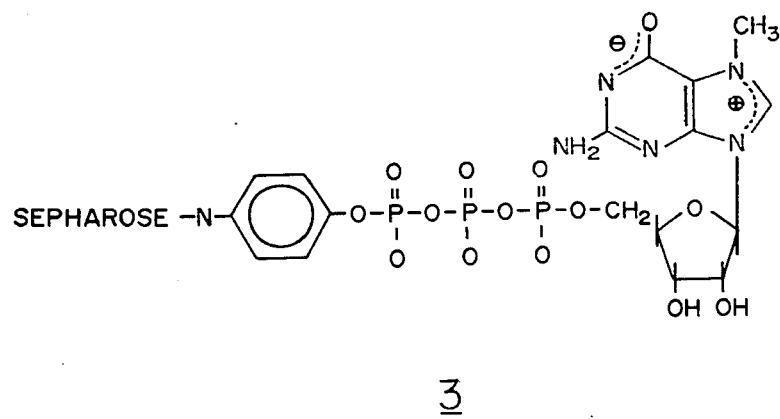

The media for affinity chromatography which are the subject of the present invention are composed of three distinct components, first, 7-methylguanosine-5'-triphosphatyl group; second, a linking agent between the γ-triphosphatyl group and the affinity chromatography support material; and third, an affinity chromatography support material. Of these three components, one, the 7-methylguanosine-5'-triphosphatyl group is invariant. It must be present in all embodiments of this invention because it is the moiety which the mRNA binding factors recognize and results in their specific affinity for the media. The other two components of the present invention can be varied. For example, the linking agent is not limited to the most preferred embodiment, the p-aminophenolic group, but could include p-aminophenolic groups substituted on the aromatic ring with one or more alkyl, halo, alkoxyl groups or combinations thereof. Linking agents of the form —NH(CHR)$_n$O where n is 1 to 6 and R represents one or more hydrogen, alkyl, halo or alkoxyl groups are also suitable.

Suitable affinity chromatography support materials are not limited to the most preferred embodiment of the present invention, Sepharose, but include coated glass beads, the diameter of said beads depending on the flow characteristics desired.

The most preferred embodiment of the present invention employs 7-methylguanosine triphosphatyl group, p-aminophenolic group as linking agent and Sepharose 4B-200 (60–140 μ bead size, exclusion limit 20×10$^6$) as support material. This most preferred embodiment is prepared according to the following example. In the following example, HPLC analysis of reaction products were performed on a Partisil-10-SAX (Whatman Chemical Separation, Inc., Clifton, NJ) bonded phase anion exchange column. In all cases, the eluting solvent was 0.4M NaH$_2$PO$_4$, pH 3.3, at a flow rate of 1.5 ml/min. DMF was dried and distilled over CaH$_2$, and p-nitrophenol was recrystallized from ethanol-water. All Sephadex chromatography was performed at 4° C.

Synthesis of m$^7$GTP-triethylammonium salt. Guanosine triphosphate (GTP) (300 mg, 0.5 mmol) was methylated using dimethyl sulfate according to the procedure of Hendler et al. ((1970) Biochemistry 9, 414) with modification. The reaction mixture was neutralized and the product purified on a DEAE Sephadex A-25 (Sephadex is a registered trademark of Pharmacia Fine Chemicals, Inc.) column (3×50 cm). The column was washed with water and then eluted with a linear gradient of 0 to 0.8M triethylammonium bicarbonate (TEAB), pH 7.8 (2 l total volume). Twenty-milliliter fractions were collected and assayed spectrophometrically at 260 nm. m$^7$GTP eluted at approximately 0.4M, and the peak was pooled and repeatedly evaporated to dryness from water vacuo. m$^7$GTP-triethylammonium salt was obtained as a white solid (0.25 mmol, 50% yield).

Activation of m$^7$GTP. This step was performed by a modification of the procedure of Knorre et al. ((1976) Feb. Lett. 70, 105). m$^7$GTP-triethylammonium salt was converted into the tri-n-octylammonium salt using tri-n-octylamine. A solution of m$^7$GTP (0.24 mmol) in methanol (5 ml) was treated with tri-n-octylamine (0.32 ml, 0.72 mmol) and stirred at room temperature until a clear solution was obtained (approximately 1 h). The solvent was evaporated under reduced pressure and the residue dried thoroughly by repeated evaporation under vacuum with dry dimethylformamide (DMF) (3×1 ml). The dried product was dissolved in anhydrous methanol:DMF (1:9 v/v. 7 ml), treated with dicyclohexylcarbodiimide (0.302 g, 1.44 mmol) and stirred overnight at room temperature in a dessicator. The solvent was evaporated at the end of the reaction.

m$^7$GTP-p-nitrophenyl-γ-ester. The activated m$^7$GTP was dissolved in dry DMF (7 ml) and treated with p-nitrophenol (0.68 g, 4.8 mmol) and triethylamine (0.65 ml, 4.8 mmol) as previously described (Knorre et al.). The reaction flask was tightly stoppered and stirred for 24 h at room temperature. The reaction mixture was then diluted with water (20 ml), cooled, and the pH adjusted to 3.5 with HCl. The mixture was washed with ether (2×25 ml) to remove unreacted p-nitrophenol. The aqueous layer was neutralized and chromatographed on a DEAE Sephadex column (1.8×45 cm). The column was washed with water and eluted with a linear gradient of 0 to 0.6M TEAB (1.2 l total volume). Fractions were assayed spectrophotometrically at 260 nm and 340 nm. Two closely spaced peaks eluted at 0.33 and 0.37M, respectively. The location of the desired p-nitrophenyl-γ-ester peak was determined by enzymatic assay of individual fractions using alkaline phosphatase and phosphodiesterase I. The release of p-nitrophenolate ion was monitored by the increase in absorbance at 405 nm. The first peak, which had a high $A_{340}$ reading, gave a negative test and was discarded. The purity of the fractions was determined by HPLC analysis. The p-nitrophenyl-γ-ester of m$^7$GTP had a retention time of 4.2 min. The peak eluting at 0.37M was pooled and repeatedly evaporated to dryness with water to give the p-nitrophenyl-γ-ester of m$^7$GTP (713 $A_{260}$ units, 0.017 mmols). The extinction coefficient of this ester is the same as that of m$^7$GTP at 260(1M~10,000.).

Reduction of p-nitrophenyl m$^7$GTP. The p-nitrophenyl-γ-ester of m$^7$GTP (700 $A_{260}$ units 0.07 mmols) was dissolved in H$_2$0 (10 ml) and reduced by the method of Berglund and Eckstein ((1972) Eur. J. Biochem 28, 492). Argon was bubbled through the solution, after which palladium on charcoal (100 mg) was added. Hydrogen was bubbled through the suspension for 3 h. The reaction mixture was then filtered and the catalyst washed repeatedly with water. The filtrate and combined washings were loaded on a DEAE Sephadex column (1×40 cm). The column was washed with H$_2$O and the product eluted with a linear gradient of 0 to 0.8M. The peak was pooled and evaporated under vacuum to give the p-aminophenyl-γ-ester of m$^7$GTP (287 $A_{260}$ units 0.029 mmols). The product was found to be essentially pure by HPLC analysis and had a retention time of 2.8 min.

Coupling to Sepharose 4B. The coupling reaction was performed by established procedures (Cuatrecasas et al. ((1968) Proc. Natl. Acad. Sci. U.S.A. 61, 536). H$_2$O (15 ml) was added to settled Sepharose 4B (15 ml). Sepharose is a registered trademark of Pharmacia Fine Chemical. The suspension was stirred and cooled to 5° C. A solution of cyanogen bromide (1.8 ml of a 1 g/ml solution) in acetonitrile was added, and the pH was maintained between 11–11.5 by addition of 1N NaOH for 20 min. The resin was then filtered and washed with H$_2$O (1 l) and cold 0.1M NaHCO$_3$—Na$_2$CO$_3$ buffer (pH 9.0, 1l). The washed resin in buffer (30 ml total volume) was treated with the p-aminophenyl-γ-ester of m$^7$GTP (287 $A_{260}$ units 0.029 mmols). The slurry was stirred overnight at 4° C. after which the resin was filtered and washed with water. An aliquot of this resin (300λ settled volume) was suspended in a buffer (1 mL) containing 0.11M Tris, 0.11M NaCl, 15 mM MgCl$_2$, pH 8.8. Alkaline phosphatase (10 units) and phosphodiesterase I (5 units) were added to release the bound nucleotide, and the change in absorbance of the supernatant fluid was followed at 260 nm (Berglund and Eckstein). The amount of bound p-aminophenyl-γ-ester of m$^7$GTP was found to be 0.18 μmol/ml (1.8 A$_{260}$ units/mL) settled Sepharose. This is subsequently referred to as m$^7$GTP-Sepharose.

Synthesis of GTP-substituted Sepharose. The p-aminophenyl-γ-ester of GTP was synthesized by the procedure outlined above. The final ester bound to Sepharose-4B was 0.29 μmol/ml resin.

Affinity purification of CBP. A 0.5M KCl extract of reticulocyte ribosomes was prepared as previously described (Hellmann et al.). The extract was precipitated using 70% saturation of ammonium sulfate, dialyzed against Buffer A (20 mM Tris-HCl, pH 7.5 at 4° C., 0.2 mM EDTA, 1 mM dithiothreitol, and 10% glycerol) containing 100 mM KCl, and passed over a column of m$^7$GTP-Sepharose (1 ml of resin per 70 mg of extract). The column was washed with 30 to 50 vol of Buffer A, and CBP was eluted with 70 μM m$^7$GTP in Buffer A. In some cases, the column was stripped with 1M KCl in Buffer A. Finally, any residual protein was removed with 0.2% sodium dodecylsulfate before reusing the affinity material. In some cases it was necessary to repass the bound fraction to obtain pure CBP.

CBP was also purified from the postribosomal supernatant fraction of rabbit reticulocyte lysate (Hellmann et al.) by essentially the same procedure. In this case 1 ml of resin was used per 100 ml of supernatant fluid.

Assay of CBP. Activity was detected by binding of oligonucleotides of the form m$^7$Gppp (Np)$_{6-8}$[$^{32}$P]pCp to protein samples and applying them to nitrocellulose filters (Hellmann et al.).

Other methods. Protein was estimated in crude fractions (ribosomal salt wash, unbound fraction) by absorption at 280 nm, and in purified fractions (bound), by the method of Bradford ((1976) Anal. Biochem. 72, 248). Gel electrophoresis of protein fractions was by the method of Laemmli and Favre ((1973) J. Mol. Biol. 80, 575), and detection, by staining with silver (Morrissey ((1981) Anal. Biochem. 117 307). Sucrose gradients were run in Buffer A containing 0.1M KCl as described previously (Hellmann et al.).

Figure 2:
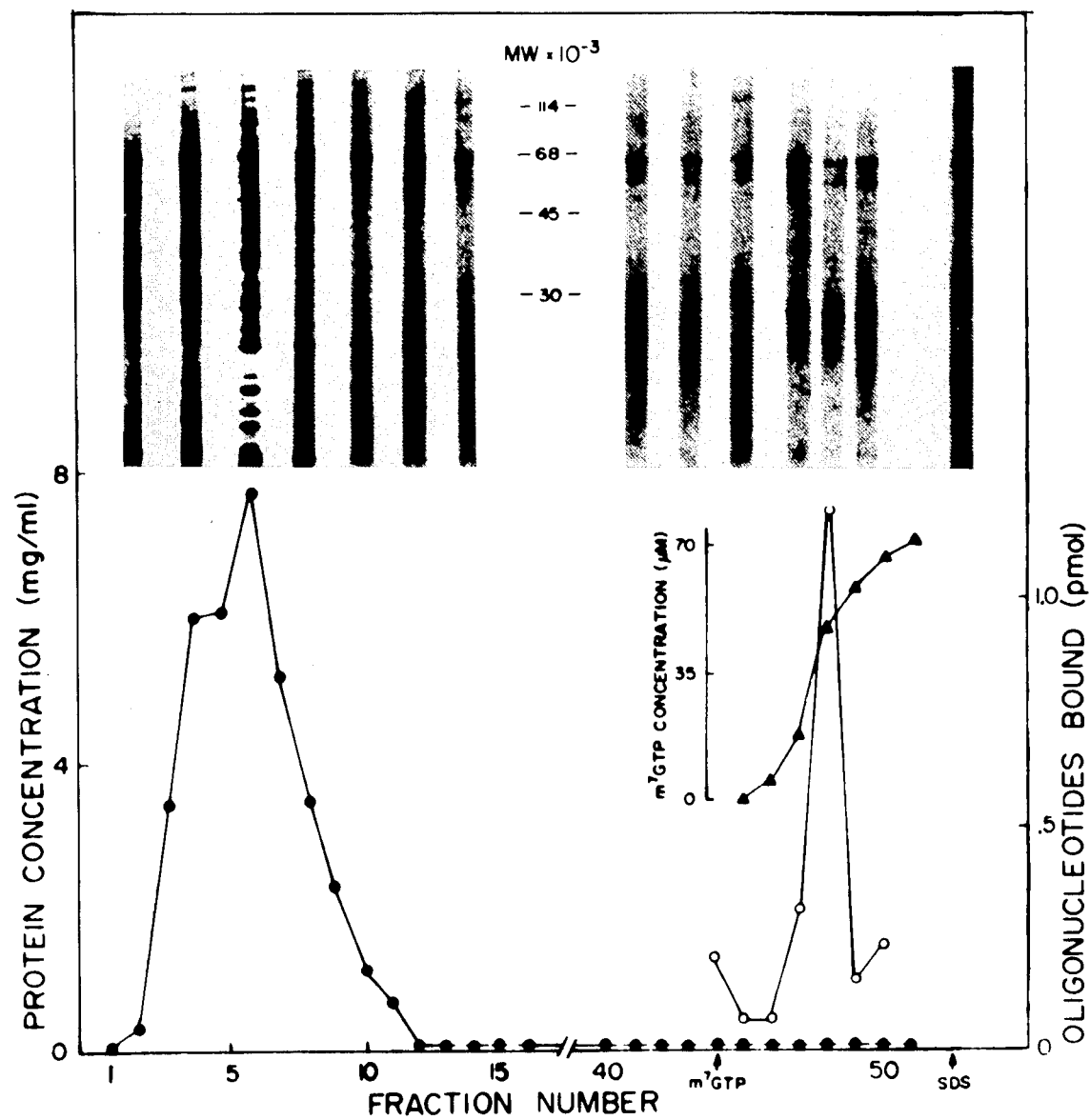
FIG. 2 is a graphical presentation of the elution of CBP from m$^7$GTP-Sepharose. The high salt ribosomal wash fraction derived from 87 ml of lysate (3.05) mg protein was applied to a 1-ml column of m$^7$GTP-Sepharose as described in the specification. At Fraction 44 (first arrow) elution was begun with 70 μM m$^7$GTP, and fractions were assayed for CBP by the oligonucleotide-binding assay. Finally, residual protein was stripped with 0.2% sodium dodecylsulfate (second arrow). o-o, oligonucleotides bound; m$^7$GTP concentration used for elution; •-• protein concentration. The inset portion of FIG. 2 presents aliquots of selected fractions were analyzed by electrophoresis with detection of protein by silver staining. The two prominent bands at approximately 50 and 65 kd are artifacts of the staining method and do not correspond to polypeptides.

Results of affinity purification studies. A crude salt wash of reticulocyte ribosomes was applied to the m$^7$GTP-Sepharose affinity medium. After extensive washing, the column was eluted with 70 μM mGTP. As shown in FIG. 2, very little of the protein was retained on the column. No protein could be detected in the m$^7$GTP-eluted fraction (first arrow) by absorption at 280 nm. By gel analysis, however, a single protein species of 24 kd could be detected. This corresponds in mobility to a protein previously identified as CBP by cross-linking to the 5'-terminus of mRNA (Sonenberg et al., (1978) Proc. Natl. Acad. Sci. U.S.A. 75, 4843), by its ability to restore protein synthesis to poliovirus-infected cell lysates (Trachsel et al.), and by its ability to reverse inhibition by cap analogues of cell-free protein synthesis (Hellmann et al., 1982). Identity of this polypeptide as CBP was further confirmed by assay with labeled, capped oligonucleotides (FIG. 2). The peak in oligonucleotide binding was coincident with appearance of the 24 kd polypeptide and occurred as the eluting m$^7$GTP was reaching a maximum concentration.

To determine whether the m$^7$GTP completely eluted CBP, the column was stripped with sodium dodecylsulfate (second arrow). While it is apparent that a considerable amount of protein was nonspecifically bound, no CBP was eluted by this treatment.

The specificity of binding was confirmed in a separate experiment. An equal quantity of ribosomal salt was applied to a control column of GTP-Sepharose, in which the nucleotide-Sepharose linkage was identical to that of m$^7$GTP-Sepharose. No polypeptide of 24 kd was eluted with m$^7$GTP, although several larger polypeptides were observed. Thus, the binding of CBP to m$^7$GTP-Sepharose appears to be by specific recognition of the m$^7$G moiety as opposed to purine ring, triphosphates, etc.

Previously, it was shown that binding of capped oligonucleotides to CBP is improved in the presence of nucleotides such as ATP or GTP and Mg++ (Hellmann et al.). Also, Sonenberg ((1981) Nucleic Acids Res. 9, 1643) has shown that in the presence of ATP and Mg++, cross-linking of the 5'-terminus of mRNA to the 24 kd CBP is reduced in favor of cross-linking to other polypeptides of 28, 50 and 80 kd. It was therefore of interest to repeat the experiment shown in FIG. 2, but in the presence of 1 mM ATP, 0.2 mM GTP and 1 mM MgCl$_2$. Only the 24 kd CBP was specifically retained by the affinity medium as before. However, the volume of 70 μM m$^7$GTP required to elute all the CBP was roughly three-fold greater than in the absence of nucleotides, suggesting a tighter binding.

Figure 3:
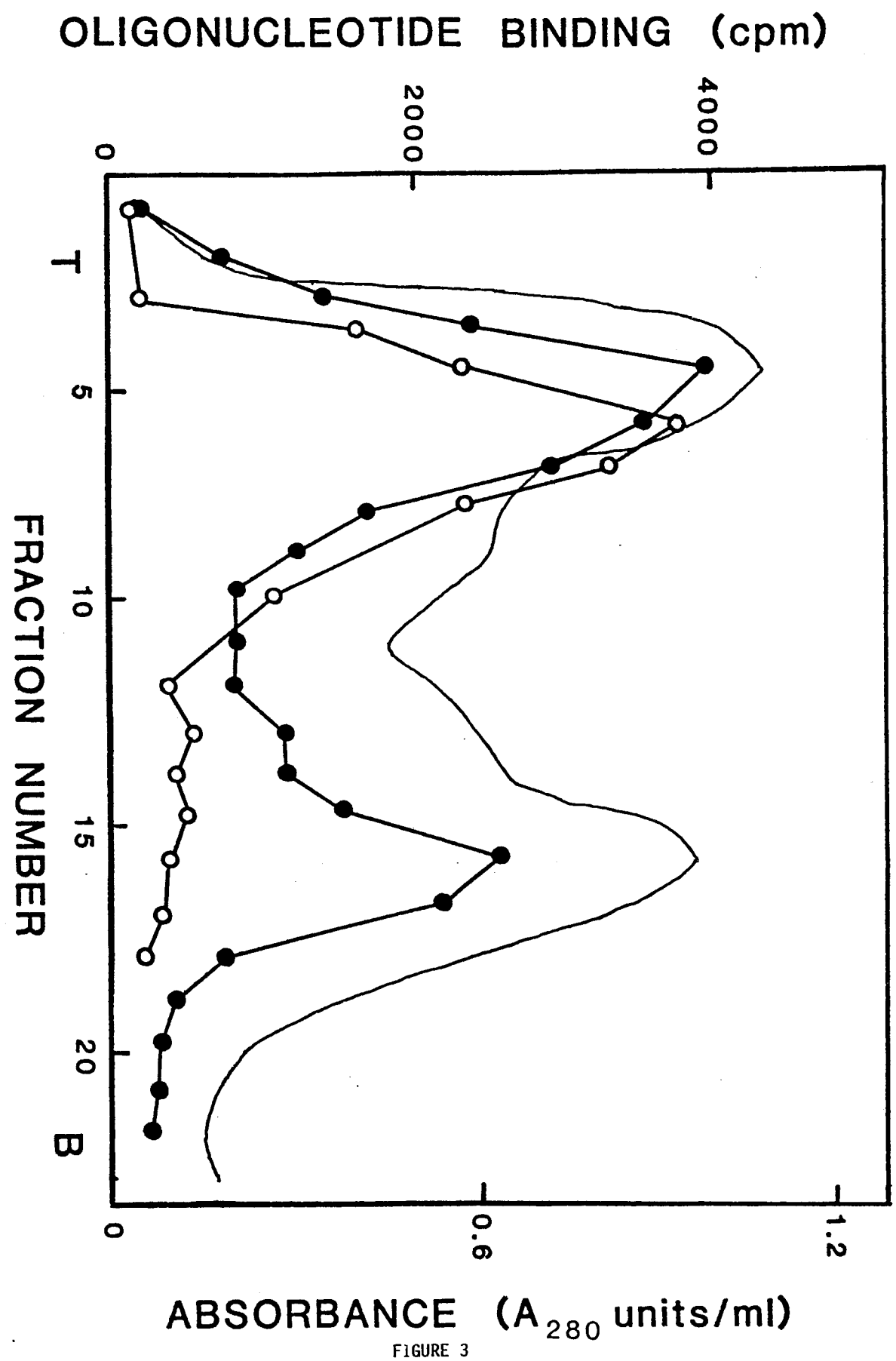
FIG. 3 is a graphical presentation of the oligonucleotide-binding activity of reticulocyte ribosomal salt wash purified through Step 3 in Hellmann et al. (1982). The protein fraction was sedimented on a 12 ml 15–30% linear sucrose gradient in a Beckman SW-40 rotor for 24 h at 35,000 rpm at 4° C. Fractions of 40μ were assayed for binding of $^{32}$P-labeled capped oligonucleotides in the absence (•-•) or presence (o-o) of competing m$^7$GTP (200 μM).

Quantitation of affinity-purified CBP. In order to estimate the yield and specific enrichment of CBP by the affinity purification, column fractions were tested by the oligonucleotide-binding assay. However, a considerable amount of nonspecific binding of capped oligonucleotides occurs with crude fractions. This is illustrated in FIG. 3, where reticulocyte high salt ribosomal wash, purified through Step 3 in Hellmann et al., was sedimented on a sucrose gradient in 100 mM KCl. Previously it has been shown that most of the CBP co-sediments with eIF-3, the faster of the two peaks (Trachsel et al. and Hellmann et al.). As shown in the figure, oligonucleotide binding occurred with both the slowly sedimenting protein and eIF-3, but only binding to the latter was blocked by the competitor m$^7$GTP. Thus, in testing crude fractions, it is essential that m$^7$GTP be employed as competitor to distinguish between specific and nonspecific binding.

The affinity-purified material was tested by oligonucleotide binding in the presence and absence of m$^7$GTP (Table 1). While the activity of the crude starting material could be inhibited only 23%, that of the purified fraction could be inhibited 91%. The unbound fraction exhibited no specific binding, indicating that all of the CBP was removed in one pass through the column. This was confirmed by passing the unbound fraction through a second affinity column and showing, by electrophoresis, that no CBP was retained. By contrast, the unbound fraction of a GTP-Sepharose column retained oligonucleotide-binding activity.

By computing the specific binding per mg of protein assayed, it was shown that the purified material was enriched 191-fold over starting material (Table 1). The recovery of activity was 44%. This may be due to the instability of CBP when extensively purified (Trachsel et al., Hellmann et al.). Also, due to the elution conditions, there was some competing m$^7$GTP present in the reaction mixtures (10–35 μM) when purified fractions were assayed; this would be expected to give an underestimate of the activity.

CBP in the postribosomal supernatant fraction. Previous purification schemes for CBP have generally started from the ribosomal salt wash of reticulocyte ribosomes (Sonenberg et al.; Trachsel et al.; Hellmann et al.). In Table 1, the results of an isolation of CBP from the postribosomal supernatant fraction is shown. Oligonucleotide-binding activity was observed in the eluted fraction, and it could be inhibited 81% by $m^7GTP$, indicating it was specific. Quantitatively there was slightly more activity than in the ribosomal salt wash. By electrophoretic analysis, the eluted material consisted primarily of the 24 kd CBP. A second affinity column purification was sufficient to remove contaminating polypeptides and leave only CBP.

We claim:

1. A compound of the formula

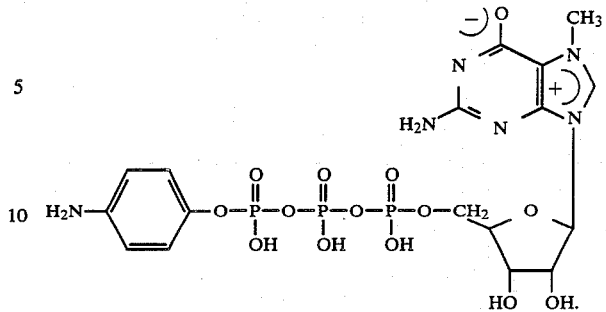

2. A compound of the formula

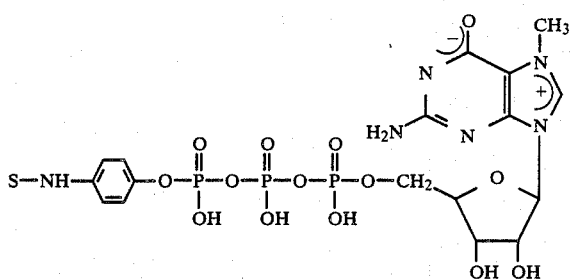

where S is Sepharose.

3. A method of isolating cap-binding protein which comprises the following steps:
   (a) passing a medium containing cap-binding protein over a column comprised of the compound of claim 2,
   (b) washing the column with buffer which is comprised of millimolar concentrations of Tris-HCL, pH approximately 7.5, ethylenediaminetetraacetic acid (EDTA), and dithiothreitol, and glycerol in the range of 10%, and
   (c) eluting the cap-binding protein from the column with a solution comprised of 7-methylguanosine-5'-triphosphate and the above described buffer.

* * * * *